US010610425B2

(12) United States Patent
Yang et al.

(10) Patent No.: US 10,610,425 B2
(45) Date of Patent: Apr. 7, 2020

(54) WRAPPING DEVICE FOR WRAPPING BODY PARTS

(71) Applicant: NATIONAL CHIAO TUNG UNIVERSITY, Hsinchu (TW)

(72) Inventors: Bing-Shiang Yang, Hsinchu (TW); Jian-Mu Lai, Kaohsiung (TW)

(73) Assignee: National Chiao Tung University, Hsinchu (TW)

( * ) Notice: Subject to any disclaimer, the term of this patent is extended or adjusted under 35 U.S.C. 154(b) by 226 days.

(21) Appl. No.: 15/620,275

(22) Filed: Jun. 12, 2017

(65) Prior Publication Data

US 2018/0280211 A1  Oct. 4, 2018

(30) Foreign Application Priority Data

Mar. 28, 2017  (TW) .............................. 106110377 A

(51) Int. Cl.
*A61F 15/00* (2006.01)
*A61F 13/04* (2006.01)

(52) U.S. Cl.
CPC ............ *A61F 15/005* (2013.01); *A61F 13/04* (2013.01); *A61F 15/007* (2013.01)

(58) Field of Classification Search
CPC .... A61F 15/002; A61F 15/005; A61F 15/007; A61F 13/04
See application file for complete search history.

(56) References Cited

U.S. PATENT DOCUMENTS

| | | | | |
|---|---|---|---|---|
| 3,547,731 A | * | 12/1970 | Curtis | ................... B29C 63/024 156/392 |
| 4,008,114 A | * | 2/1977 | Lindsey | ............... B65H 23/063 156/392 |
| 4,055,171 A | * | 10/1977 | Ries | ......................... A61F 5/04 602/22 |
| 4,058,427 A | | 11/1977 | Wilson | |

(Continued)

FOREIGN PATENT DOCUMENTS

| CN | 2033672 U | 3/1989 |
|---|---|---|
| CN | 201085719 Y | 7/2008 |

(Continued)

*Primary Examiner* — Michael E Gallion
(74) *Attorney, Agent, or Firm* — Muncy, Geissler, Olds & Lowe, P.C.

(57) ABSTRACT

The present invention provides a wrapping device for wrapping body parts. Said wrapping device comprises a rotation module having a first roller ring, a second roller ring, and a plurality of connecting parts; a driving module driving at least one of the first roller ring and the second roller ring to revolve; and at least a pressing device disposed on the second roller ring. In said wrapping device, the first roller ring and the second roller ring are separately and coaxially disposed, while the opposite ends of each of the plurality of connecting parts are separately connected to the first roller ring and the second roller ring. In addition, the first roller ring includes a first ring hole surrounded and formed by a first inner ring wall, and the second roller ring includes a second ring hole surrounded and formed by a second inner ring wall. Said at least a pressing device protrudes toward an inner space of the second ring hole.

14 Claims, 11 Drawing Sheets

(56) References Cited

U.S. PATENT DOCUMENTS

| | | | | |
|---|---|---|---|---|
| 6,440,245 B1* | 8/2002 | Culzoni | ............... | B29C 63/06 |
| | | | | 156/187 |
| 8,100,290 B2 | 1/2012 | Bizzell et al. | | |
| 9,445,956 B1* | 9/2016 | Trapani | ............... | A61F 15/005 |
| 2007/0068837 A1* | 3/2007 | D'Angelis | ............ | A61F 15/002 |
| | | | | 206/440 |
| 2010/0216359 A1* | 8/2010 | Samelian | ............... | B63C 9/082 |
| | | | | 441/81 |
| 2019/0365554 A1* | 12/2019 | Davies-Sekle | ....... | A61H 1/0281 |

FOREIGN PATENT DOCUMENTS

| | | |
|---|---|---|
| CN | 201328908 Y | 10/2009 |
| CN | 201831995 U | 5/2011 |
| CN | 202198716 U | 4/2012 |
| CN | 202724060 U | 2/2013 |
| CN | 202859405 U | 4/2013 |
| CN | 204521246 U | 5/2015 |
| CN | 205586152 U | 9/2016 |
| TW | I508696 | 11/2015 |

* cited by examiner

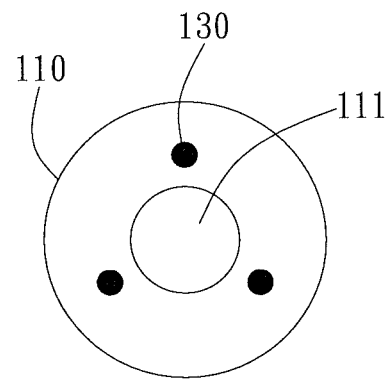
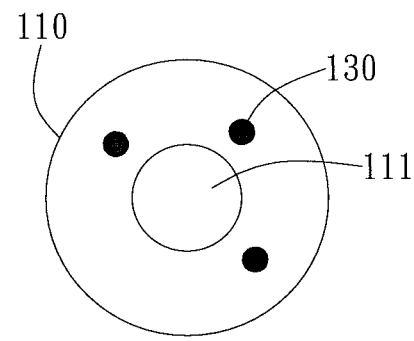
FIG. 3A  FIG. 3B
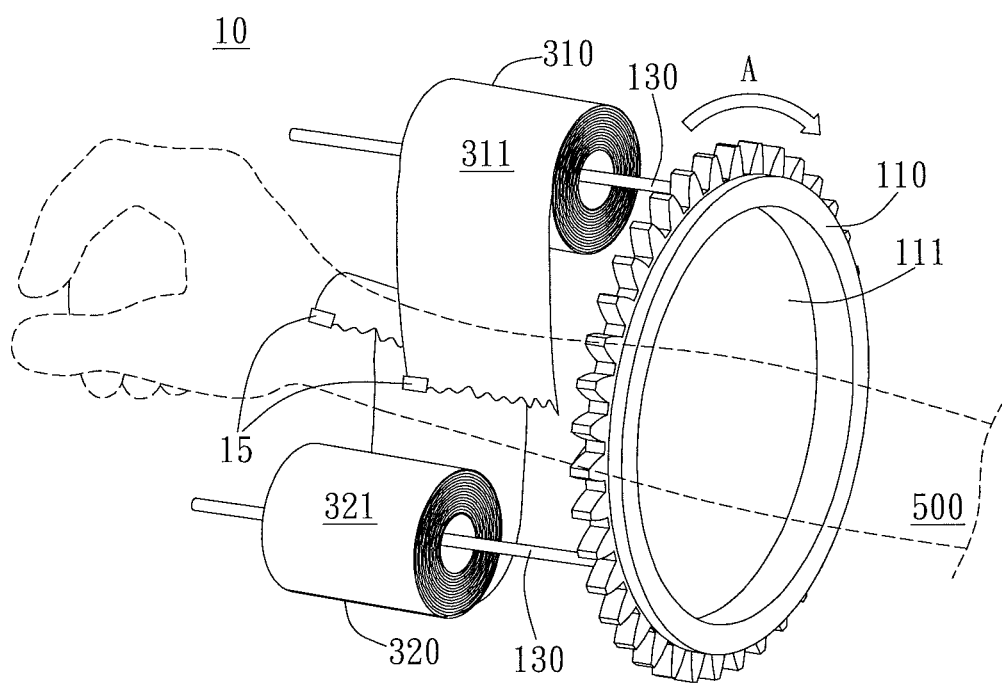
FIG. 4

WRAPPING DEVICE FOR WRAPPING BODY PARTS

PRIORITY

The present invention claims priority to the Application No. 106110377 filed on Mar. 28, 2017 in Taiwan (ROC), which was entitled "WRAPPING DEVICE FOR WRAPPING LIMBS". All of which are hereby incorporated by reference as if fully set forth herein.

FIELD OF INVENTION

This invention generally relates to a wrapping device for wrapping body parts. Specifically, the present invention relates to a wrapping device for wrapping body parts with wrapping materials.

BACKGROUND

In the medical field, bandaging a wound or an affected area of a patient has always been one of the important work of medical staffs. However, bandaging is time consuming and laborious, and qualities of the bandaging results are usually uneven based on the experience and the skills of the operated medical staff Therefore, qualities of the medical treatments subjected to the patients are not stable, such that the patient's experience and the final medical effect are not stable. Further, the time-consuming and laborious bandage works might also delay and affect the treatment of other patients in a critical state.

For example, in the treatment of fractures, it is necessary to fix a broken bone in place for fracture healing. In general, the most widely used method of bone fixation is the gypsum fixation, which is also commonly known as the plaster cast bandage. The gypsum fixation can be used for mild or moderate bone deformation. In the case of the severe bone deformation that requires surgery, gypsum fixation can also be used to treat the body parts before/after a surgery so as to prevent further dislocation of the bones, or the inserted members loosening. However, currently the plaster cast bandage mainly implemented by manual work, and it takes 20-30 minutes and requires 2-3 medical staffs involved in the whole process. Thus, the gypsum fixation is generally a crucial clinical work in the emergency departments and the outpatient departments, and it consumes a lot of time and effort in the medical field. In viewing of the foregoing, medical staff shortage or insufficient treatment time would likely to cause poor quality of plaster cast, so as to reduce the quality of medical care, or even lead to further medical harm to the patients in the treatment.

Nowadays, although there are several fixation methods which take less time than the gypsum fixation, the techniques are not yet mature and need to be refined. For example, in such devices that cover the affected area with flexible objects and inflate the gasbag to affix/fix the affected area, it is easily to cause the affected area to irritation, injury, or infection, characterized by pain, redness, swelling due to the poor ability of fixation. Also, such devices are easily taken off by the patients, which consequently is not conducive to the recovery of the affected area. Moreover, such fast-fit devices are mostly personal disposable devices, so that the unit price/is higher than the standard gypsum fixation. It therefore make the patients or the medical units to bear a greater cost. Thus, in practical experience, if it is not an urgent situation or convenience is not the most important priority for the treatment, most of the medical staffs will still choose the gypsum fixation method implemented by the bandaging and wrapping.

As described above, in order to preserve the advantages of the gypsum fixation method and to reduce the manpower needs, it is necessary to develop a device or a method for efficiently wrapping the bandage and reducing the time implemented in the bandaging and wrapping.

SUMMARY OF THE INVENTION

Technical Means for Solving the Problems

To solve the above issues, an embodiment of the present invention provides a wrapping device for wrapping body parts. Said wrapping device comprises a rotation module having a first roller ring, a second roller ring, and a plurality of connecting parts; a driving module driving at least one of the first roller ring and the second roller ring to revolve; and at least a pressing device disposed on the second roller ring. In said wrapping device, the first roller ring and the second roller ring are separately and coaxially disposed, while the opposite ends of each of the plurality of connecting parts are separately connected to the first roller ring and the second roller ring. In addition, the first roller ring includes a first ring hole surrounded and formed by a first inner ring wall, and the second roller ring includes a second ring hole surrounded and formed by a second inner ring wall. Said at least pressing device protrude toward an inner space of the second ring hole.

Technical Effects Achieved by the Technical Means

The wrapping device for wrapping body parts according to an embodiment of the present invention is capable of automatically or semi-automatically winding the bandage on the wound or the affected area of body parts in a regular or irregular shape, thereby reducing the manual labour and the implementation time required in the bandaging and wrapping. Furthermore, the wrapping device is capable winding several required bandages in one bandaging procedure, thus simplifying the cumbersome process of wrapping different types or layers of bandages at the same time.

BRIEF DESCRIPTION OF THE DRAWINGS

FIGS. 3A and 3B are configuration views of the connecting parts according to embodiments of the present invention.

FIG. 4 is a schematic view of wrapping using a wrapping device according to an embodiment of the present invention.

DETAILED DESCRIPTION OF THE PRESENT INVENTION

Figure 1:
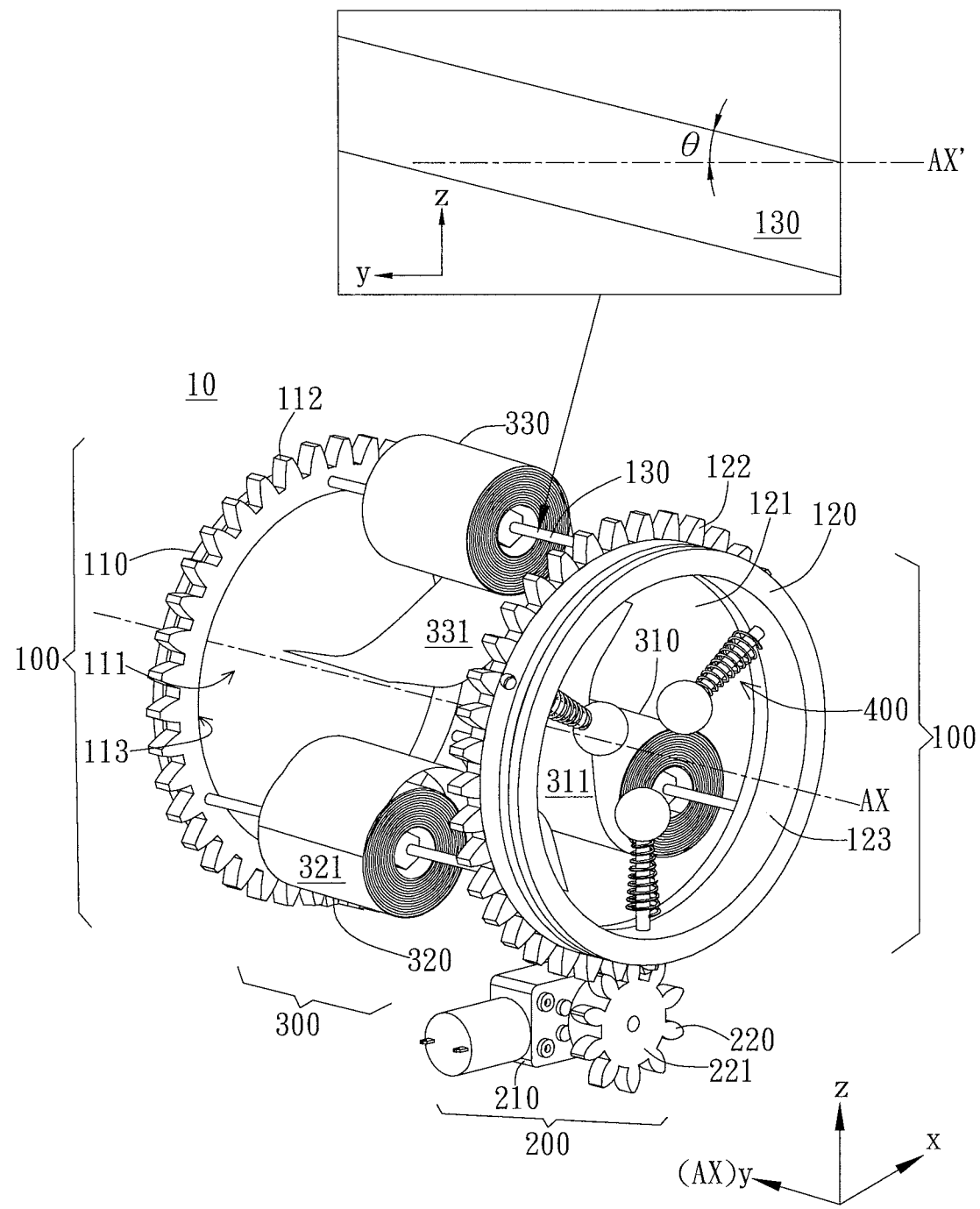
FIG. 1 is a schematic view of a wrapping device according to an embodiment of the present invention.
Figure 2A:
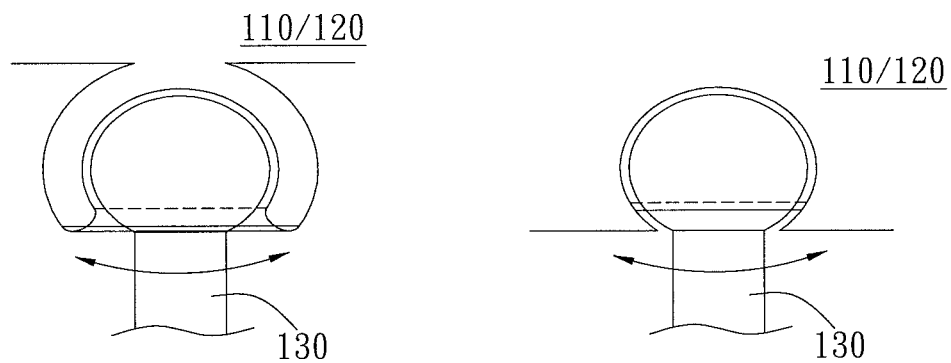
FIGS. 2A and 2B are schematic views showing a connection end structure of the connecting parts according to embodiments of the present invention.
Figure 2B:
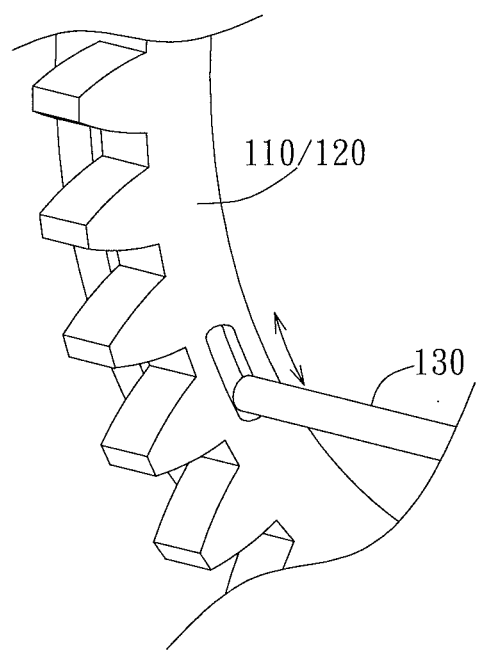

The present invention will be described more fully hereinafter with reference to the accompanying drawings, in which exemplary embodiments of the invention are shown. In the drawings, the thickness of layers and regions may be exaggerated or otherwise modified for clarity. The same or similar reference numerals in different drawings represent the same or similar elements. Furthermore, well-known structures, materials, or operations are not shown or described in detail to avoid obscuring aspects of the described devices. As those skilled in the art would realize, the described embodiments may be modified in various different ways, all without departing from the spirit or scope of the present invention. It should be noted that, without conflict, in the embodiment of the present invention and examples of features can be combined with each other. Therefore, it should be appreciated that the embodiments described herein are not intended to be exhaustive of all possible embodiments in accordance with the present disclosure, and that additional embodiments may be conceived based on the subject matter disclosed herein.

A wrapping device 10 according to an embodiment of the present invention will be described with reference to FIGS. 1 to 3B.

First, referring to FIG. 1, a wrapping device 10 according to an embodiment of the present invention includes a rotation module 100, a driving module 200, and at least one pressing device 400. Said rotation module 100 includes a first roller ring 110 and a second roller ring 120 disposed coaxially and separately with respect to each other, and a plurality of connecting parts 130 respectively connecting the first and second roller rings 110 and 120 at both ends. The first roller ring 110 includes a first ring hole 111 surrounded and formed by a first inner ring wall 113, and the second roller ring 120 includes a second ring hole 121 surrounded and formed by a second inner ring wall 123. According to the embodiment of the present invention shown in FIG. 1, in the wrapping device 10, the size of the first ring hole 111 and the second ring hole 121 are designed such that the body parts (such as limbs) can pass therethrough. In another preferred embodiment, the size of the first ring hole 111 and the second ring hole 121 are designed such that the limb joint, such as an ankle and an elbow, are capable of being nested. However, the present invention is not limited thereto, and the sizes of the first ring hole 111 and the second ring hole 121 may be set as required.

In the wrapping device 10, the driving module 200 drives at least one of the first roller ring 110 and the second roller ring 120 to rotate. Here, the first roller ring 110 and the second roller ring 120 are shown in a circular shape. However, the first roller ring 110 and the second roller ring 120 may be of any shape as long as they can be driven by the driving module 200 in various ways, such as circular, rectangular, oval, hexagonal, triangular or irregular shape, and the present invention is not limited to the embodiments shown herein.

According to a preferred embodiment, the driving module 200 may include a motor 210, and a driving gear set 220 having at least one gear 221. In the preferred embodiment described above, for example, a biaxial motor having a biaxial capable of driving different objects simultaneously can be used, so as to drive the first roller ring 110 and the second roller ring 120 simultaneously. However, the present invention is not limited thereto, and the present invention may use other motors to drive one of the first roller ring 110 and the second roller ring 120, and then to drive the other one of the first roller ring 110 and the second roller ring 120 by the connecting part 130 through mechanical linkage. In the preferred embodiment, the first roller ring 110 and the second roller ring 120 may further have external tooth structures 112 and 122, respectively. When the driving module 200 is operated, the motor 210 drives the rotation of the driving gear set 220, and at least one gear 221 of the driving gear set 220 is engaged with at least one of the external tooth structures 112 and 122 of the first roller ring 110 and the second roller ring 120, so as to drive and rotate the first roller ring 110 and the second roller ring 120 by the motor 210. However, this is merely an example, and the present invention is not limited thereto. For example, other embodiments of the present invention may also include other driving modules 200 of non-motor and gear configurations as long as the first roller ring 110 and the second roller ring 120 are capable of rotation.

The driving module 200 according to an embodiment of the present invention may further include electronic components such as other transmission parts, control boards, power lines, etc. required for driving. Regarding the details of the internal structure of the driving module 200 described above, it will be appreciated by those of ordinary skill in the art upon reading this disclosure that the driving module 200 can be any device for driving and certain changes or modifications may be made without departing from the spirit or scope of the disclosure. Thus, the explanation of the internal structure of the driving module 200 is omitted herein and will not specifically stated.

Next, in the wrapping device 10 shown in FIG. 1, said at least one pressing device 400 is provided on the second roller ring 120 and protrudes toward an inner space of the second ring hole 121. Specifically, said at least one pressing device 400 is provided on the second inner ring wall 123 and protrudes toward an inner space of the second ring hole 121. Here, three pressing device 400 protruding from the second inner ring wall 123 toward the center of the second ring hole 121 are shown. However, the number and arrangement of the pressing device 400 of the present invention are not limited thereto. For example, the pressing device 400 may be provided on the other portion of the second roller ring 120 and extend into an inner space of the second ring hole 121. In addition, the wrapping device 10 may include one or more pressing devices 400. The various embodiments and quantities of the pressing devices 400 will be further described in detail hereafter.

In addition to the rotation module 100, the driving module 200 and the at least one pressing device 400, the wrapping module 300 may be further included in the wrapping device 10 shown in FIG. 1. According to a preferred embodiment of the present invention, the wrapping module 300 may include three wrapping material rolls 310-330 positioned and nested axially on the three connecting parts 130, respectively, and the cores of the wrapping material rolls 310-330 may further comprise a structure such as a base in aid of positioning the wrapping material rolls 310-330 on the connecting parts 130. Here, the connecting parts 130 and the bases may be respectively different circular cylinders, polygonal cylinders, non-geometrically consistent continuous cylinders, non-solid, and non-integrally assembled objects, and the present invention is not limited thereto.

Here, said wrapping material rolls 310-330 respectively includes wrapping materials 311-331 wound into a roll form.

According to the above description with respect to FIG. 1, the wrapping device 10 comprises three connecting parts 130 and three wrapping material rolls 310-330 respectively nested and located within a certain range on the three connecting parts 130. However, FIG. 1 is merely an example, and according to other embodiments of the present invention, the wrapping device may include one, two, three, four, or even five or more connecting parts and wrapping material rolls.

In addition, in the embodiment shown in FIG. 1, although the same number of connecting parts and wrapping material rolls are contained, according to another embodiment of the present invention, the number of connecting parts and the number of wrapping material rolls included in the wrapping device 10 might be different. For example, the wrapping device may comprise four connecting parts, and only two of them are each provided with a wrapping material roll; or the wrapping device may comprise two connecting parts, and one of them is provided with a wrapping material roll, and the other one is provided with two wrapping material rolls respectively disposed on different portion of the connecting part fore-and-aft. In addition, the same or different wrapping material rolls may be provided at different distances or the same distance in different connecting parts fore-and-aft.

The connecting parts 130 of the wrapping device 10 are inclined with a deviation angle θ with respect to the axis AX passing through the centers of the first roller ring 110 and the second roller ring 120. Specifically, when the axis AX passing through the centers of the first roller ring 110 and the second roller ring 120 is the Y-axis direction, the gravity direction is the Z-axis direction, and the direction perpendicular to the Y-axis direction and the Z-axis direction along the tray surfaces of the first roller ring 110 and the second roller ring 120 is X-axis direction, the connecting parts 130 can be offset obliquely along both the X-axis direction and the Z-axis direction from a virtual line AX' parallel to the axis AX, such that they are inclined with a deviation angle θ respectively with respect to each X, Y, and Z-axis directions.

Further, the connection ends of the connecting parts 130 and one of the first roller ring 110 and the second roller ring 120, or the connection ends of the connecting parts 130 and both first roller ring 110 and second roller ring 120 may include a structure in which the deviation angle θ of the connecting parts 130 can be changed within a preset range. Specifically, at least one endpoint of the connecting parts 130 at two roller rings may have a degree of moving freedom within a preset range, and two endpoints of a connecting part 130 may have different degrees of moving freedom. Accordingly, the movements of two endpoints of the connecting part 130 differ from each other, thereby generating the deviation angle θ. That is, according to an embodiment of the present invention, the deviation angle θ of the connecting part 130 can be changed with respect to the irregular wrapping-targeted body parts, and the deviation angle θ of the connecting part 130 can be adjusted during operation. For example, the deviation angle θ may be adjusted based on the speed of the wrap or the speed of advancement.

In a preferred embodiment of the present invention, the deviation angle θ may be altered instantaneously in accordance with the surface shape of the object in real-time. For example, referring to FIG. 2A and FIG. 2B, in connection with FIG. 1, the connection end structure that the deviation angle θ of the connecting part 130 can be altered within a preset range may be a ball and socket joint shown in FIG. 2A or a groove shown in FIG. 2B. In detail, the connection ends of the connecting part 130 attached on the first roller ring 110 and the second roller ring 120 are respectively provided with a preset degree of moving freedom, and for example are movable in one direction (as arrows shown in FIG. 2A and FIG. 2B indicated) with the degree of moving freedom.

In another preferred embodiment of the present invention, the degree of moving freedom for the connecting part 130 at two axially opposite directions are different. That is, the connecting part 130 may have a different degree of moving freedom at the connection ends respectively attached to the first roller ring 110 and the second roller ring 120, and thereby the connecting part 130 with different degree of moving freedom at two ends is capable of being adjusted in accordance with the body parts along with the applied force direction during wrapping, so that a desired specific deviation angle θ can be generated instantaneously in real-time. However, the present invention is not limited to the ball and socket joint or the groove described above, and any structure in which the connecting part 130 is not detached while maintaining a certain degree of moving freedom to change the deviation angle θ within a preset range can be used instead.

According to the wrapping device of the embodiment of the present invention, the connecting parts 130 disposed between the two roller rings may be evenly or unevenly distributed with respect to each other. For example, reference is made to FIG. 3A and FIG. 3B in connection with FIG. 1, in which FIG. 3A and FIG. 3B show the distribution of the connecting parts 130 seen from the tray surface of the first roller ring 110. In FIG. 3A, the connecting parts 130 are distributed at the same separate distance and angles with respect to each other. In FIG. 3B, different from FIG. 3A, the connecting parts 130 are distributed at different separate distance and angles with respect to each other. In fact, in a preferred embodiment, the connecting parts 130 may be detachable and capable of being detached from the whole wrapping device 10. Thus, the factors such as the distribution, separate distance and angles of the connecting part 130 can be variated and modified in accordance with the actual demand.

Hereinafter, a method for wrapping the body parts using the wrapping device 10 shown in FIG. 1 will be briefly described with reference to FIG. 4 to FIG. 6. In the following description, the proportions of the structure and the body parts are adjusted for clarity and do not represent the actual relative proportions. In addition, in order to avoid unnecessary obscurity, the details of the partial structure and the reference numerals of some element will not be specifically shown.

According to an embodiment of the present invention, FIG. 4 shows a schematic view in body parts wrapping using the wrapping device 10. First, referring to FIG. 4, a targeted body part 500 such as an al n is initially put into the wrapping device 10 from the first ring hole 111, and the unfolded end of the wrapping material rolls 310-330 can be manually attached on the side adjacent to the affected area intended to be wrapped with a tape. Next, the driving module 200 is actuated to rotate the first roller ring 110 and the second roller ring 120 along the arrow direction A, such that the connecting parts 130 would rotate around the body part 500 along with the rotation of the first roller ring 110 and the second roller ring 120. As described above, the wrapping material rolls 310-330 mounted and nested on the connecting parts 130 would unfold the folded wrapping materials 311-331 along with the rotation of the connecting parts 130, and the unfolded wrapping materials 311-331 would be wound around the targeted position sequentially.

During wrapping, the distance or the length of the body part 500 put into the wrapping device 10 can be adjusted by the patient in accordance with the actual demand, or otherwise the medical staff may adjust the position of the wrapping device 10 to achieve the similar effect. Further, the body part 500 and the wrapping device 10 can also be moved at the same time. Accordingly, the wrapping sequence of the wrapping material rolls 310-330 may be determined in accordance with the relative movements of the body part 500 and/or the wrapping device 10, and the wrapping sequence can be altered instantaneously in real-time according to the demands. As stated above, during moving the body part 500 or the wrapping device 10, the wrapping material may be wound on the body part 500 layer by layer at a helix angle. However, the present invention is not limited thereto, and the body part can be wound with various angle and manner based on the arrangement of the wrapping material rolls (Such as the wrapping material rolls 310-330), and the relative movement of the body part 500 and the wrapping device 10.

In an embodiment of the present invention, the driving module 200 of the wrapping device 10 may have different driving modes, such that the rotation module 100 may have various rotation modes, such as different rotation speeds, rotation rhythm and rotation force etc. Patients and medical staffs can adjust the driving modes to wrap in accordance with the demands at any time during wrapping the body part 500.

Next, several possible aspects of wrapping at the affected area during the wrapping using the wrapping device 10 of the present invention will be described with reference to FIG. 5A to FIG. 5C.

Figure 5A:
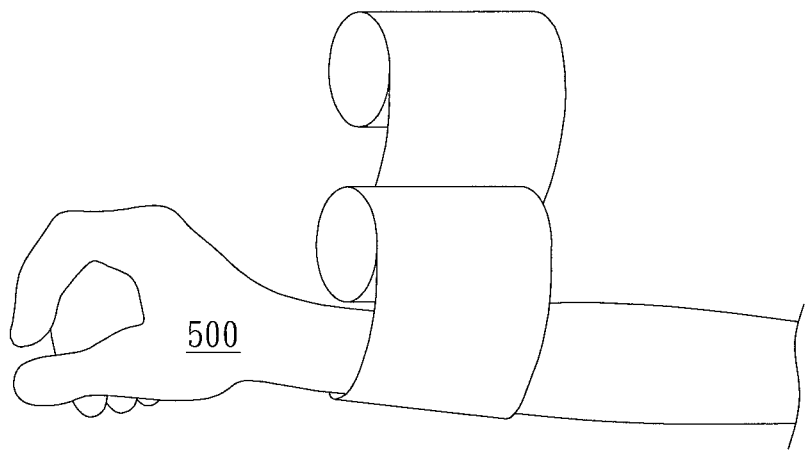
FIGS. 5A to 5C are schematic views of different wrapping aspects of the wrapping device according to embodiments of the present invention.

Referring to FIG. 5A, in an embodiment of the present invention, bandage rolls in the front and rear are wound sequentially in the same direction, and the coverage range thereof are substantially overlapping with each other. That is, with a time difference, a wrapping material of a later wrapping material roll would directly overlap the wrapping material of a previous wrapping material roll wound before. For example, when winding two rolls of cotton rolls, two layers of bandages can be wound on the same place by this manner, so as to reach the required bandage thickness while reducing the required connecting part length and the required corresponding space for disposing different wrapping material roll in the wrapping device. In addition, it is possible to increase the number of the wrapping material rolls that can be disposed in the wrapping device. In this case, for example, the wrapping material rolls 310 and 320 positioned at different connecting parts 130 can be disposed at the same separate distance from the first roller ring 110.

Figure 5B:
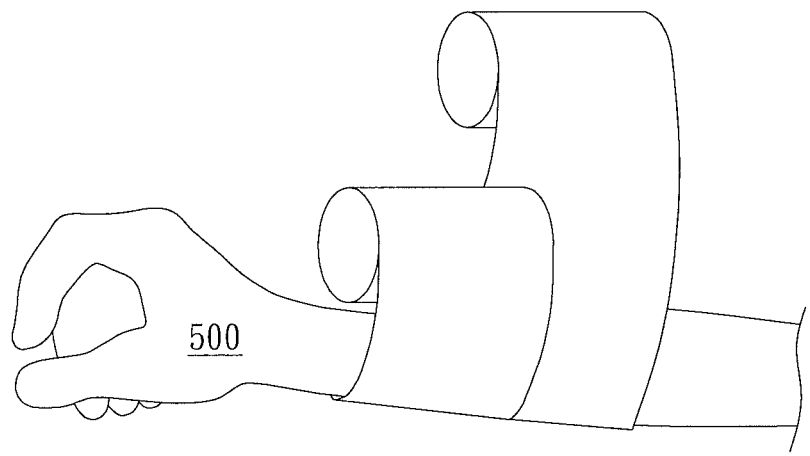

Next, referring to FIG. 5B, in another embodiment of the present invention, different from the embodiment of FIG. 5A, although the bandage rolls in the front and rear are also wound sequentially in the same direction, the coverage range thereof are only partially overlapping with each other. For example, when winding two rolls of cotton rolls, this manner can accelerate the progress for wrapping the same required area of the body part, so as to improve the wrapping efficiency. Also, it will improve the appearance of the bandaging since the boundary line between each circle of bandage around the body part 500 is less obvious. In this case, for example, the wrapping material rolls 310 and 320 located in the different connecting parts 130 may be disposed at different separate distances from the first roller ring 110.

Figure 5C:
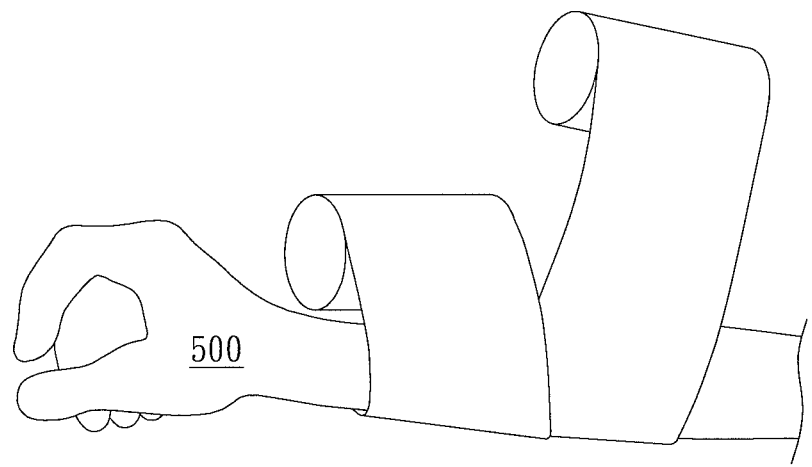

Next, as shown in FIG. 5C, in further embodiment of the present invention, different from the embodiments of FIG. 5A and FIG. 5B, the bandage rolls in the front and rear are wound sequentially in different direction. That is, by adjusting the deviation angles of different connecting parts 130, the different wrapping material rolls 310 and 320 located on different connecting parts 130 may have different directionality or angle. By the above manner, the wrapping can be implemented in specific directionality or angle (such as cross angle) with respect to the desired wrapping form. In this case, for example, the wrapping material rolls 310 and 320 located on different connecting parts 130 may be disposed at different separate distances from the first roller ring 110 and corresponding angles.

The wrapping aspects described above with reference to FIG. 5A to 5C are merely illustrated as examples, and as person having ordinary skill in the art would understand, various desired wrapping state can be achieved by adjusting the angle of the connecting parts, the type and the number of the wrapping material roll, the relative separate distance of the wrapping material roll etc., and the present invention is not limited to the above-described examples.

Figure 6:
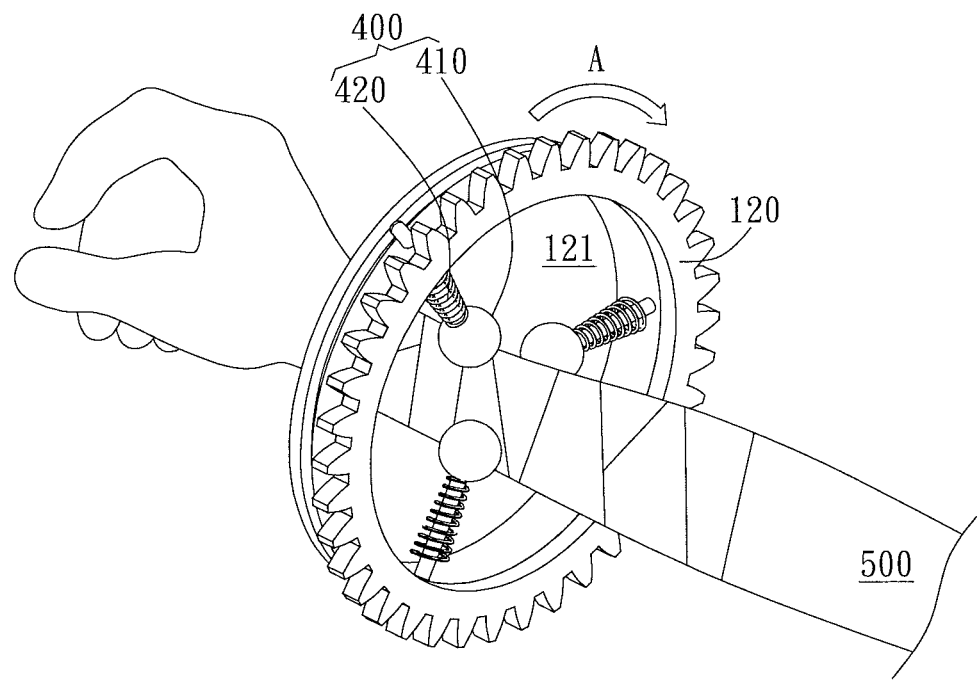
FIG. 6 is a schematic view of wrapping using a wrapping device according to an embodiment of the present invention.

Then, referring to FIG. 6, when the bandaged body part 500 passes through the second ring hole 121 of the second roller ring 120, the pressing device 400 mechanically linked to the second roller ring 120 is rotated along with the second roller ring 120, so as to smoothen the bandaging, and to make the surface of the wound wrapping materials to smoothly modified with respect to the structure contours for regular or irregular body part 500. That is, the wrapping materials can be pressed to be flattened by the pressing device 400 along with the shape of the body part 500.

After finishing the wrapping, the medical staff or patients can manually tailor the end of the bandage to complete the wrapping. However, the present invention is not limited thereto. In another preferred embodiment of the present invention, a slidable blade may also be provided at the outlet end of the bandage of the wrapping device to guide the bandage, and may slide and cut the bandage at suitable length. In the above case, the timing of tailor can be determined further by the dressing thickness (the dressing thickness can be measured by sensing manner or the dressing thickness can be set according to the preset rotation circles) or the bandage tension.

In the embodiment shown in FIG. 6, the pressing device 400 includes a pressing end 410 connected to and supported by the spring structure 420, wherein the pressing end 410 is proximity to the center of the second ring hole 121 and the two ends of the spring structure 420 are respectively connected to the pressing end 410 and the second inner ring wall 123. As described above, when a pressing ball served as the pressing end 410 contacts the body part 500, the spring structure 420 is compressed or stretched as the pressing ball is pressed against the irregular body part 500, and the pressing ball at the pressing end 410 will press the bandage or the wrapping materials wound on the body part 500 with the spherical contact surface. Upon rotating the first roller ring 110 and the second roller ring 120, the pressing device 400 mechanically linked to the roller ring can thereby be rotated about the body part 500, such that the pressing device 400 can smoothen and modify the wrapping materials with the spherical contact surface by the elastic force of the spring structure 420 along the peripheral contour of the body part 500. Therefore, the regular or irregular body part 500 may be wrapped in a more compliant manner by the wrapping device 10.

In a preferred embodiment of the invention, the spring structure 420 of the pressing device 400 may have a support member (not shown) for supporting, a spring member (not shown) for compression and stretch. In such embodiment, the spring member is mainly used to adjust the distance between the pressing end and the second inner ring wall, while the support member is used to reduce the possible deformation of the spring member.

The structure and the number of the pressing device 400 described above are merely examples, and the present invention is not limited thereto. Specifically, any structure that can smoothen and modify the appearance of wrapping along the contour of the body part can be applied in the wrapping device of the present invention in any amounts.

Figure 7A:
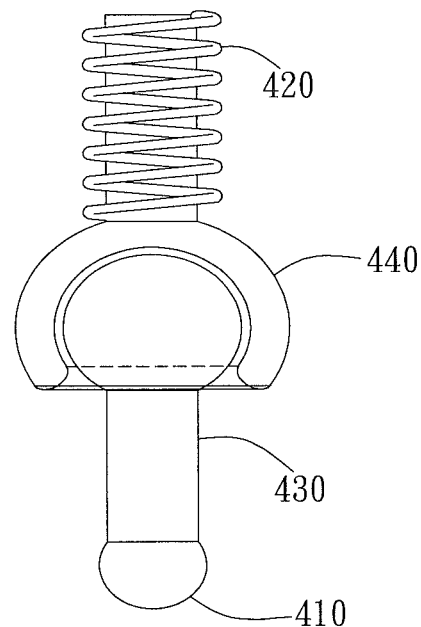
FIGS. 7A to 7D are schematic views of various pressing devices according to embodiments of the present invention.
Figure 7B:
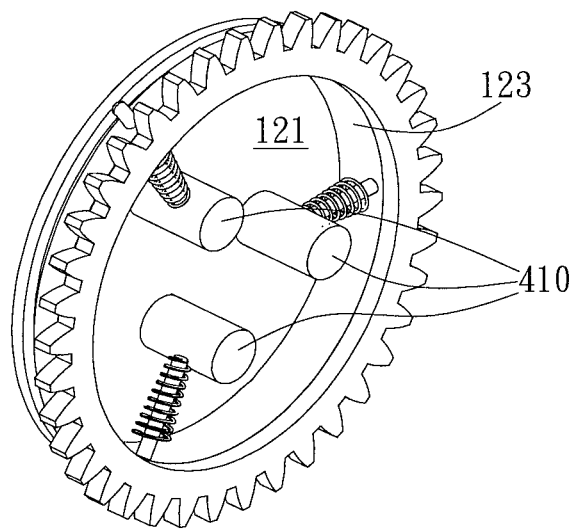
Figure 7C:
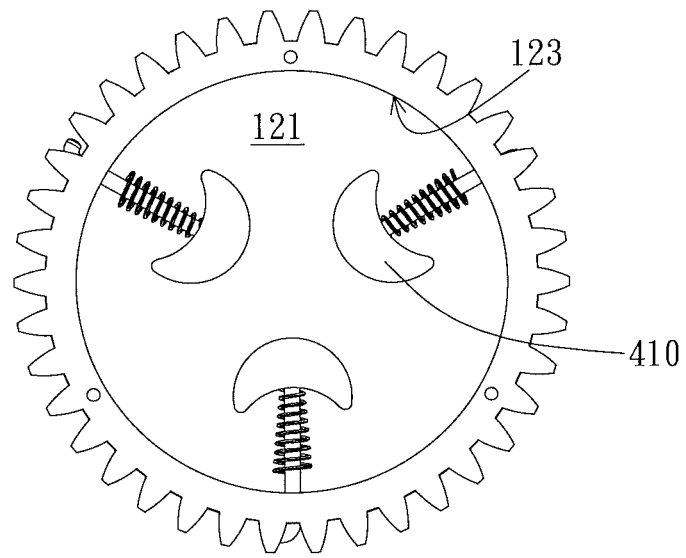

For example, with reference to FIG. 7A, the pressing end 410 may be hemispherical or partially spherical in shape, rather than to be complete spherical in shape as shown in FIG. 6, and the pressing end 410 may be attached to the spring structure 420 through a ball and socket joint 440 with a connecting rod 430. In the above embodiment, a certain degree of moving freedom provided by the ball and socket joint 440 can further improve the smoothness of the pressing operation of the pressing device 400. In addition, in yet another modified embodiment of the present invention, referring to FIG. 7B, the pressing end 410 may be a pressing roller instead of the pressing ball as shown in FIG. 6, and only one pressing device 400 is provided for the second ring hole 121. Further, referring to FIG. 7C, the pressing ball can also be replaced by a curved flexible pad. Alternatively, a structure (not shown) similar to the scraper may also be used to instead the pressing ball. In such embodiments, the structure similar to the scraper may have a blunt edge to smoothly lie along the body part.

Figure 7D:
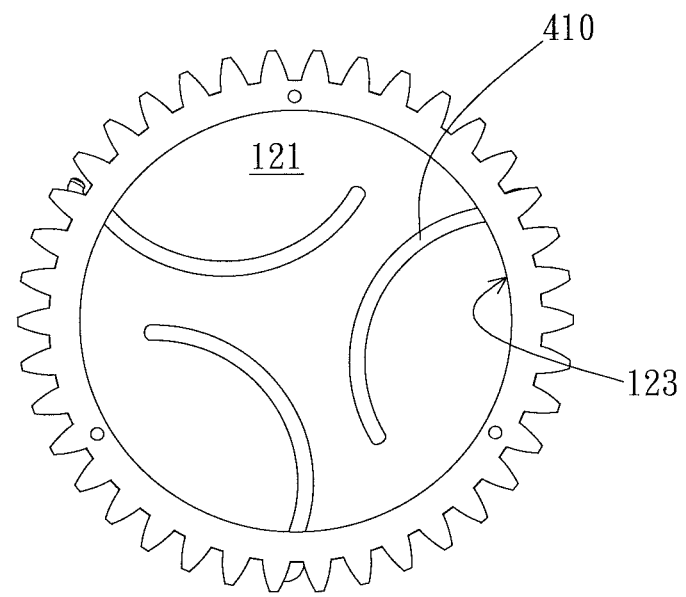

Moreover, the pressing device 400 may not be radially and vertically distributed in the inner space of the second ring hole 121, or the pressing device 400 may not be radially operated with respect to the pressing surface. For example, referring to FIG. 7D, the pressing device 400 may be a curved structure made of the materials having preset elasticity, such as metal, plastic, and/or fabric. According to the embodiment shown in FIG. 7D, the pressing device 400 may protrudes from the second inner ring wall 123 of the second ring hole 121 toward the center of the second ring hole 121 and then reflex in a parabolic form. As described above, in this embodiment, the pressing device 400 may contact the body part with the curved surface at the valley peak of the parabolic trajectory. The pressing device 400 can smooth the wrapping surface by its own elasticity with the curved surface upon rotating with the second roller ring 120. In addition, although not specifically shown, the pressing device 400 may be a brush-like structure, such that the pressing device 400 can smooth the wrapping materials wound on the wrapping surface by gently brushing along the outer peripheral contour of the body part 500.

According to the functional characteristics and requirements of the pressing device 400, 1, 2, 3, 4, 5, 10, 20, 30, 40, 50, 60, 70, 80, 90, or even more than 100 pressing devices 400 can be provided. Besides the stated numbers, any amount of the pressing devices 400 between these values can be provided. For example, when the pressing device 400 is a soft plastic strip or a paper strip similar to a brush, more than 100 pressing devices 400 can be densely provided.

In the above description, the covered body part may be, for example, part of palm, wrist, forearm, elbow, upper arm, foot, calf, knee, thigh, etc., and the present invention is not limited thereto. Moreover, in addition to directly put the body part into the first ring hole 111 of the first roller ring 110 of the wrapping device 10, the wrapping progress can be initiated by assembling the wrapping device 10 directly at the targeted body part or the affected area manually. Here, the wrapping device 10 is detachable and assemblable.

The process of body part wrapping using the wrapping device 10 stated above is merely an example, and the wrapping device and the wrapping method of the present invention may have numerous variations without departing from the spirit and principles of the present invention.

According to an embodiment of the present invention, the above-described operation can be applied to the gypsum fixation. In detail, the wrapping material rolls 310-330 may be respectively a cotton roll, a gypsum roll, and a gauze roll in sequence. In the gypsum fixation, the cotton material of the cotton roll can protect the skin, the gypsum plaster of the gypsum roll can be immobilized so as to fix the bone, and the gauze material of the gauze roll can organize and optimize the appearance of the wrapping area. As described above, when the wrapping device 10 is used for wrapping, the cotton material would cover the body part first, such that the body part is prevented from contacting the gypsum plaster directly. Therefore, the skin is protected. Then, the wetted gypsum plaster would cover the body part wound with the cotton material. Finally, the gauze material cover the body part wound with the gypsum plaster to complete the gypsum fixation.

In general, in the gypsum fixation, if it takes too much time to wrap, it might lead to an unintended adhesion and assembly of the wetted gypsum roll. As described above, by the wrapping device 10, it can significantly reduce the time and effort required for the wrapping process, thereby reducing the risk of adhesion and assembly that might occur in the gypsum roll.

According to the above gypsum fixation, in order to wrap the cotton roll, the gypsum roll and the gauze roll for bandaging respectively on the body part 500, the wrapping material rolls 310-330 positioned on three different connecting parts 130 may disposed on different locations on the connecting parts 130 fore-and-aft. For example, the wrapping material roll 310 which is a cotton roll is proximity to the first roller ring 110 than other wrapping material rolls, the wrapping material roll 330 which is a gauze roll is proximity to the second roller ring 120 than other wrapping material rolls, and the wrapping material roll 320 which is a gypsum roll may be disposed between the wrapping material roll 310 and the wrapping material roll 330. However, the above statement is merely an example, and in the gypsum fixation or other wrapping process, each factor such as type, number, location and separate distance of the wrapping material roll can be adjusted based on the actual demand. For example, different wrapping material rolls located on different connecting parts 130 may disposed at the same separate distance from the first roller ring 110.

For example, in a modified embodiment of the present invention for the gypsum fixations, more than two cotton rolls may be mounted in the wrapping device 10, and the gypsum roll is disposed far from the cotton rolls. By the above manner, before the gypsum roll is wound on the body part, an appropriate thickness of the cotton materials is ensured with enough circles of wrapping, and the risk of contamination between the wetted gypsum roll and the cotton roll can be reduced. In another modified embodiment of the present invention for gypsum fixation, three cotton rolls can be mounted in the wrapping device 10, after the wrapping of the cotton roll on the body part is finished, another wrapping device mounted with the gypsum roll can be used, or the gypsum roll can be re-mounted in said wrapping device 10 for the following wrapping. After the wrapping of the gypsum roll is finished, the wrapping of the gauze roll can be implemented in a similar way described above.

As stated above, a desired sufficient thickness of the wrapping materials wound on the body part can be ensured, such that a desired function performed by wrapping each wrapping material can be achieved. However, the embodiments of the present invention are not limited thereto, and the type, number and distribution of the wrapping material rolls in the wrapping device can be adjusted in accordance with the factors such as the actual demands and the thickness of the wrapping material that actually need to be wound. For example, the wrapping material rolls can include the same or different bandages or wrapping materials for medical treatment. Specifically, bandages or wrapping materials for medical treatment may include cotton roll, the gypsum roll, cohesive elastic crepe bandage, non-cohesive elastic crepe bandage, cotton cloth, gauze cloth, glass fabrics, etc.

In the case where the wrapping device 10 of the embodiment of the present invention is applied to the gypsum fixation, since the gypsum rolls are usually wet, the wrapping device 10 may also be designed to be water resistant. For example, waterproof electronic parts can be used, or separate plate can be used to isolate the driving module 200, the gypsum roll or other non-gypsum wrapping material rolls. The design of the water resistance can also be applied to any other situations that water resistance is necessary for bandaging. In a preferred embodiment, the modules of the different blocks can be individually arranged to achieve waterproofing. With the above configuration, for example, it may reduce the possible damage of the wetted gypsum roll to the internal structure of the wrapping device.

Hereinafter, other modified embodiments of the wrapping devices will be described by mainly taking the gypsum fixation as an example. However, it is to be understood by those of ordinary skill in the art that the present invention is not limited thereto, and various embodiments of the wrapping devices described below may be applied to every available wrapping procedure.

Figure 8:
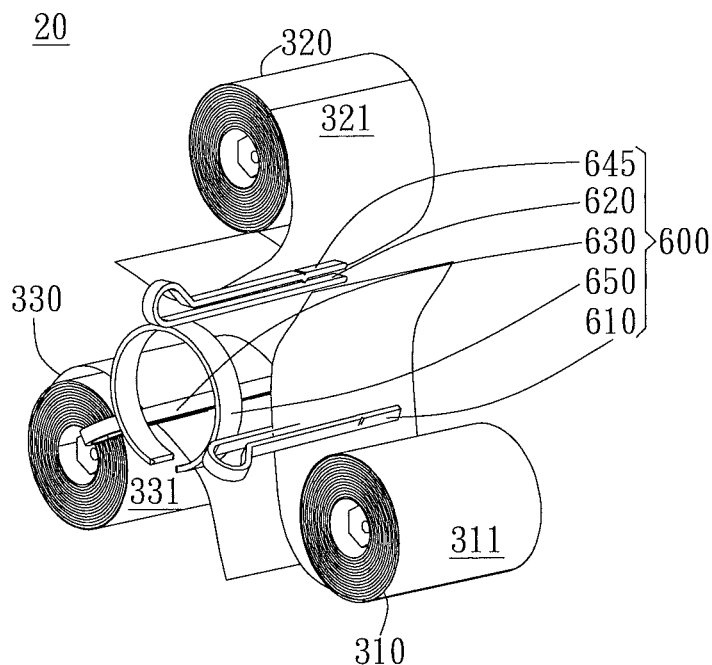
FIG. 8 is a schematic view of a fasten module in a wrapping device according to another embodiment of the present invention.

In order to fix a bandage or a wrapping material that may not be viscous, apart from manually fixing the unfolded end of the wrapping material roll with tapes, in the wrapping device 20 according to another modified embodiment of the present invention, the fasten module 600 may be further used to assist in securing the unfolded end. 8, Referring to FIG. 8, the difference between the wrapping device 20 and the wrapping device 10 is that the wrapping device 20 further comprises a fasten module 600. Here, only parts related to the fasten module 600 will be shown and explained in detail, other configurations that are the same or similar like those in the wrapping device 10 will be omitted for the sake of brevity and convenience. As described above, the fasten module 600 of the wrapping device 20 in FIG. 8 comprises a flexible collar 650, and three fasten clips 610, 620 and 630 fixedly attached to the flexible collar 650. According to the arrangement, the flexible collar 650 may be disposed proximate to the first roller ring 110, and may be disposed directly adjacent to the first roller ring 110 or may be disposed at a certain distance from the first roller ring 110 provided that it will not interfere the rotation of the first roller ring 110. The flexible collar 650 is provided so that the body part put into the wrapping device 20 from the first ring hole 111 may pass through the flexible collar 650. It is to be noted that according to the arrangement, the flexible collar 650 does not rotate with the rotation module when the wrapping device 20 is operated.

The clamping part 645 of said three fasten clips 610, 620 and 630 attached to the flexible collar 650 may protrude from the flexible collar 650 and may be substantially perpendicular to the torus of the flexible collar 650. The flexible collar 650 and the three fasten clips 610, 620 and 630 may be disposed on the portion of the body part to be wrapped at beginning, and the clamping part 645 of said fasten clips 610, 620 and 630 may clamp and fix a starting part of the unfolded end of each wrapping material rolls or the bandage. At this arrangement, the body part will initially pass through the flexible collar 650. After that, the rotation module is actuated to wrap upon respectively clamping the starting parts of different wrapping material rolls or bandages by said fasten clips 610, 620 and 630. After finishing the wrapping, the flexible collar 650 can be removed from the body part or the wrapping device 20, such that said fasten clips 610, 620 and 630 attached to the flexible collar 650 may be removed together from the body part at the site that is initially wrapped. After removing the flexible collar 650 and the fasten clips 610, 620 and 630, the start end of the wrapping material roll or the bandage that is covered and fixed by the upper layer of the wrapping material roll or the bandage is remained.

Next, a wrapping device 30 according to a further modified embodiment of the present invention will be described with reference to FIG. 9 and FIG. 10. Comparing to the wrapping device 10 shown in FIG. 1, an accommodation module 700 is further included in the wrapping device 30 shown in FIG. 9. The accommodation module 700 houses the structure of at least part of wrapping device 30. Specifically, the accommodation module 700 may include a first housing part 710 at least partially accommodating the first roller ring and enclosing a first opening 711 corresponding to the first ring hole 111, and a second housing part 720 at least partially accommodating the second roller ring and enclosing the second opening 721 corresponding to the second ring hole 121. In addition, the accommodation module 700 may further include a connecting housing part 730 located between the first and second roller rings and connecting the first housing part 710 and the second housing part 720, respectively. Here, the connecting housing part 730 is located outside the same side of the first opening 711 and the second opening 721.

In a preferred embodiment, the connecting housing part 730 also accommodates the driving module 200 to prevent the driving module 200 from being exposed. However, the present invention is not limited thereto, and the accommodation module 700 may include other housing parts for accommodating the driving module 200.

As stated above, the accommodation module 700 may further improve the appearance of the entire wrapping device 30, and may contribute to the integrity of the wrapping device 30 for operation of the patients and the medical staffs. Further, the wrapping device 30 with the accommodation module 700 may also reduce the possible contamination to the internal structure due to the wrapping material rolls. For example, when using the gypsum roll, it is capable to reduce unnecessary contamination of the gypsum to the structure of the wrapping device 30 including the driving module 200, the first roller ring 110, the second roller ring 120, and the like. In addition, the accommodation module 700 can also improve the water resistance of the integral wrapping device 30, and isolate and protect the wrapping device 30 from various factors that may damage the wrapping device 30.

Figure 9:
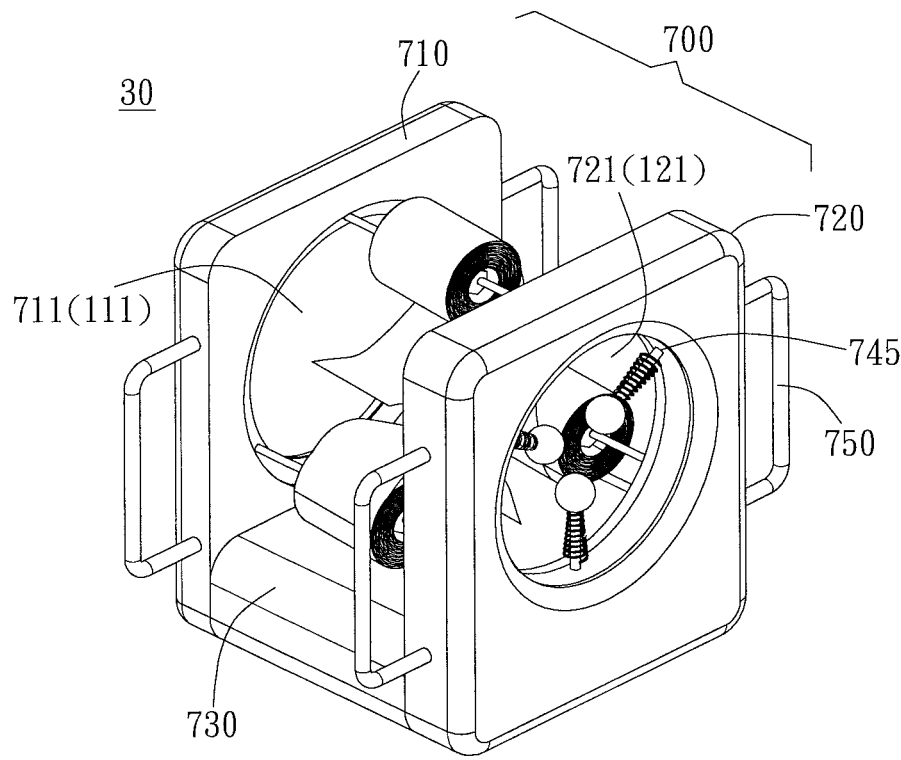
FIGS. 9 and 10 are schematic views of an accommodation module in a wrapping device according to another embodiment of the present invention.

In the wrapping device 30 shown according to FIG. 9, the accommodation module 700 may further include a through hole 745 provided on a portion of the second housing part 720 enclosing and forming the second opening 721, so that the pressing device 400 can thereby protrudes from the second housing part 720 toward the second opening 721.

Moreover, in the wrapping device 30, the accommodation module 700 may further include handles 750. For example, the handle 750 may be disposed on the outside of the first housing part 710 and/or the second housing part 720. The handle 750 may be protruded from the first housing part 710 and/or the second housing part 720, and may be a separate component or may be integrally formed with the first housing part 710 and/or the second housing part 720. In an embodiment of the present invention, the handle 720 may be disassembled and is capable of being removed from or mounted in the accommodation module 700. Here, the handle 750 shown in FIG. 9 is merely an example, and the wrapping device 30 of the present invention may contain no handle, 1 handle, 2 handles, 3 handles, or more than 4 handles. In addition, the shape and form of the handle are not limited by the handle 750 shown in FIG. 9, and various designs can be applied for the convenience of the operator to use the wrapping device 30.

In accordance with the design of the accommodation module 700, apart from the above stated protection function, the wrapping device 30 can be easily used by directly being set on a table or other similar platform when understaffed. Moreover, the handle 750 is designed so that the wrapping device 30 of the present invention can be held in the hand (Hand-held), therefore the patients or the medical staff can easily move the wrapping device 30 in place for operation convenience. Further, the wrapping device 30 can be more easily held and used by intuitively adjusting the angles thereof at will. As mentioned above, these designs further improve the applicability, convenience and reliability of the wrapping device for use.

In order to allow the first roller ring 110 and the second roller ring 120 accommodated in the accommodation module 700 to be rotated, structures such as a track and a slide rail roller can be further designed. Said structures are described in detail with reference to the partially enlarged view of the wrapping device 30 shown in FIG. 10, in which some of the structures will be omitted for the sake of clarity.

Figure 10:
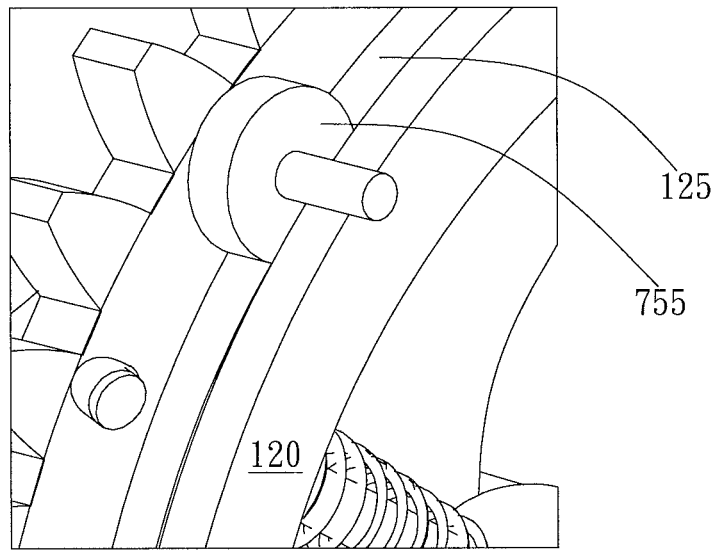

In FIG. 10, the accommodation module 700 includes a slide rail roller 755 in the first housing part 710 and/or the second housing part 720, and the outer peripheral surface of the first roller ring 110 and/or the second roller ring 120 includes a track 125, such that the slide rail roller 755 can be disposed in the track 125 and can rotate along the track 125. Here, for convenience, only the second roller ring 120 is described as an example. As stated above, as shown in FIG. 10, when the second roller ring 120 is rotated around the axis, the slide rail roller 755 will move along the track 125, and the side of the slide rail roller 755 opposite to the track 125 may contact against the second housing part 720. Thereby, the second housing part 720 can securely accommodate and fix the second roller ring 120, while still retaining the rotation capacity of the second roller ring 120.

It is to be understood by those of ordinary skill in the art that the description of the second roller ring 120 may also be applied to the first roller ring 110, and the description of the first roller ring 110 is not repeated here.

If the wrapping device 30 shown in FIG. 9 and FIG. 10 is provided with the first roller ring 110 and the second roller ring 120 having the external tooth structures 112 and 122, the external tooth structures 112 and 122 may be separately disposed from the track 125 on the outer surface of the first roller ring 110 and the second roller ring 120 in a direction parallel to the edge width. For example, in the case of the second roller ring 120, the second roller ring 120 may be an assembly of a sub-roller ring including the external tooth structures 122 and another sub-roller ring including the track 125, or the second roller ring 120 may be a structure integrated with a sub-roller ring including the external tooth structures 122 and another sub-roller ring including the track 125. However, the present invention is not limited thereto, and the designs of the external tooth structure and the track can be independently implemented, and/or may be implemented in conjunction with other structures.

Figure 11:
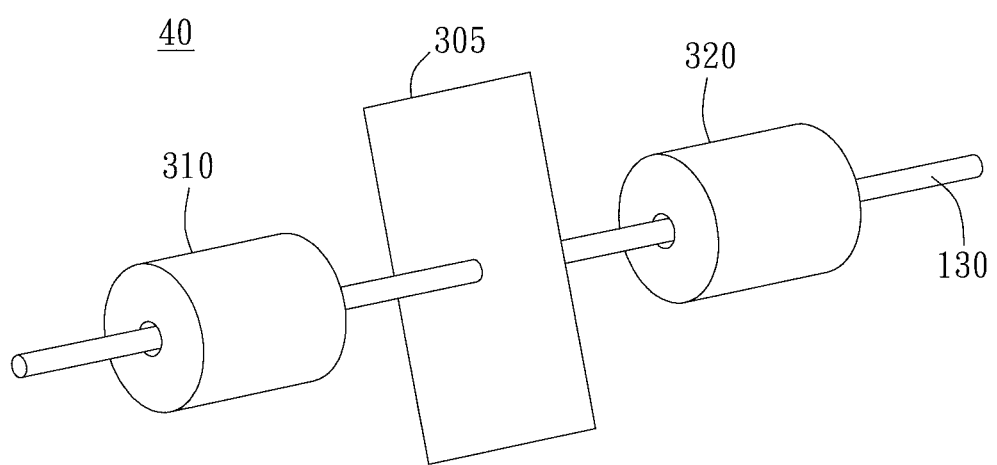
FIGS. 11 to 14 are schematic views of various shields and tension-adjusting devices according to other embodiments of the present invention.

In a wrapping device 40 according to yet another modified embodiment of the present invention, the wrapping module 300 may further comprise a shield disposed between two of the wrapping material rolls. For example, referring to FIG. 11, when two wrapping material rolls 310 and 320 are nested on the same connecting part 130, the shield 305 might be mounted on the connecting part 130 and might be a baffle plate which is position adjustable and fixable on the connecting part 130. In addition, in the wrapping device 50 according to a further modified embodiment of the present invention, referring to FIG. 12, the shield 305 might be two clamping pieces 301 and 302 clamping the roll body of the wrapping material rolls 310. According to other variations of the embodiment shown in FIG. 12, the shield 305 might be one clamping pieces 301 covering a part of the roll body, or might be one clamping pieces 302 covering a part of the roll body.

By means of the shield 305, the wrapping devices 40 and 50 may further enhance the independence of each wrapping material roll, thereby reduce the possible cross-contamination. For example, in the case of gypsum fixation, the wetted gypsum of the wetted gypsum roll might unintendedly contaminate other wrapping material or the internal structure. As described above, such contamination and damage can be relatively reduced by the shield 305.

Further, the shield 305 may be detachable, and may be removed to be cleaned. For example, referring to FIG. 12, the wrapping device 50 includes a fastener 306. The fastener 306 can fix the clamping pieces 301 and 302 on the fastening pillar 307, and the clamping pieces 301 and 302 can also be detached from the fastening pillar 307, such that it is more convenience to clean the wrapping device. In addition, in some embodiments, the clamping pieces 301 and 302 may also be integrally formed without being fixed by means such as the fastener 306 or the like.

The embodiments described above with respect to FIG. 11 and FIG. 12 are merely examples, and the shield 305 of the present invention may comprise any structure which is useful in separating or protecting the wrapping material rolls or other components.

Next, according to some modified embodiments of the present invention, in order to enable the wrapping device to adjust the tension for different wrapping material rolls or different shapes of body parts, tension-adjusting device might be further included. As described above, referring to FIGS. 12 to 14, a plurality of tension-adjusting devices 800 or 900 can be respectively disposed corresponding to and separated from the respective connecting part at preset distances, wherein each of the plurality of tension-adjusting devices 800 or 900 might have the same or different degree of tension adjustment. Specifically, in the situation that the connecting part is provided with the wrapping material roll, the tension-adjusting devices 800 or 900 may be provided in conjunction with respective one wrapping material roll or some wrapping material rolls, and the tension-adjusting devices 800 or 900 can adjust the degree of tension adjustment for different wrapping material rolls based on the needs. For example, in gypsum fixation, the gypsum roll and the normal cotton roll may require different tension adjustment parameters, even may require different tension-adjusting devices.

Figure 12:
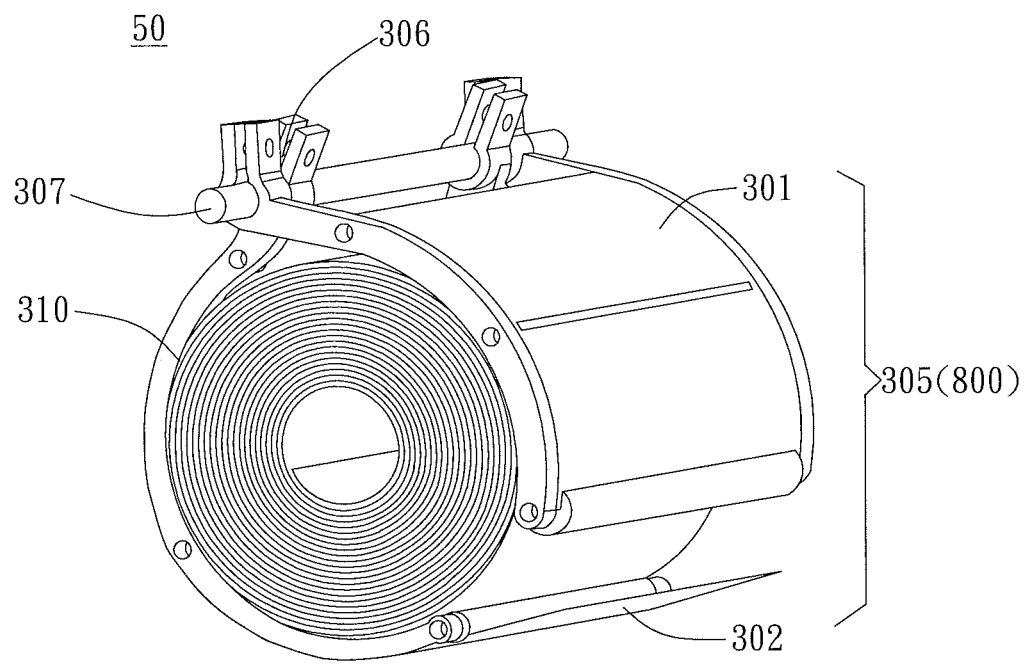

In detail, for example, referring to FIG. 12, the shield 305 of the wrapping device 50 may also be used as the tension-adjusting device 800. Here, the clamping pieces 301 and 302 are fixed through the elasticity exerted by the fastener 306, or the clamping pieces 301 and 302 are fixed due to the elasticity exerted by themselves in accordance with the material property, such that the two clamping pieces 301 and 302 is capable of being clamped toward each other and grip the bandage or the wrapping material roll to exert a pressure on the bandage or the wrapping material roll. Through this arrangement, when the bandage or the wrapping material roll is extended and unfolded from the portion of the roll body that is not clamped by the clamping pieces 301 and 302, one end is subjected to a pressure to generate the desired tension.

Figure 13:
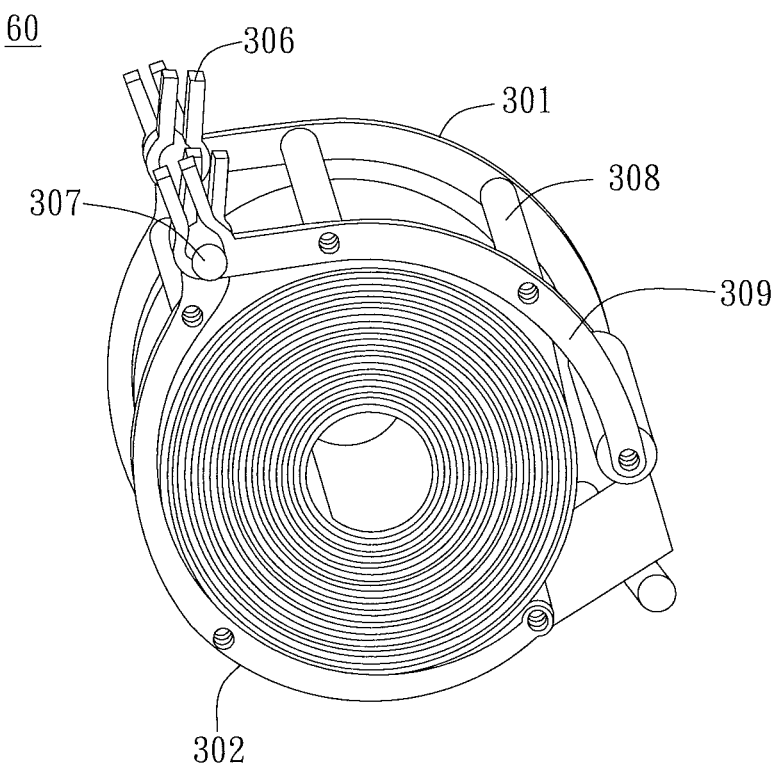
Figure 14:
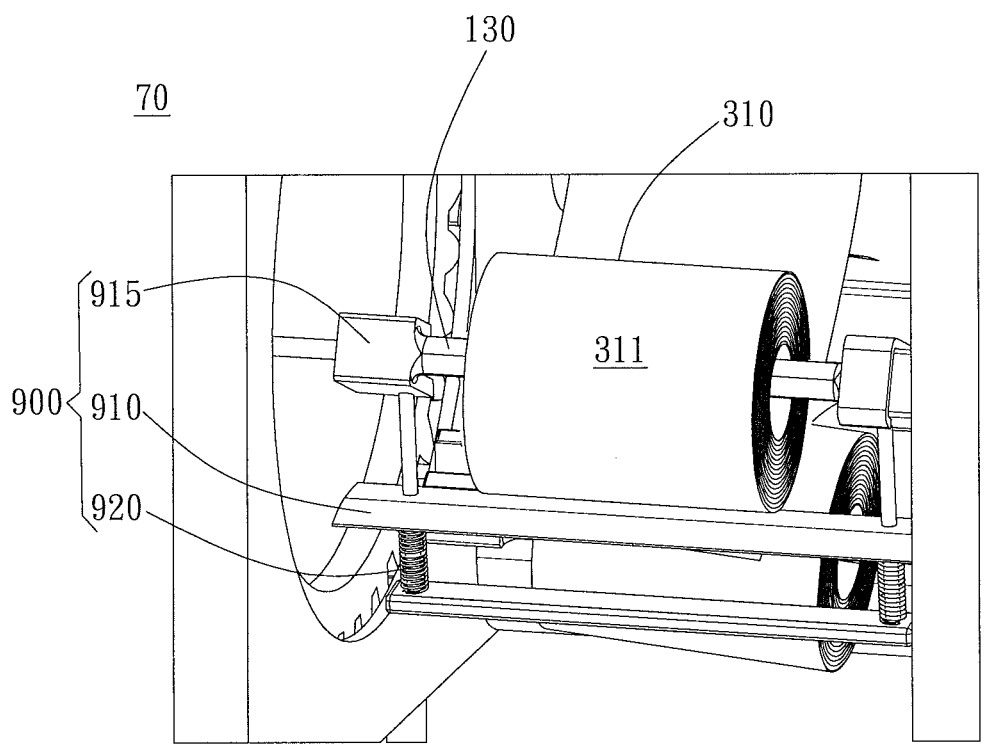

In order to remain and provide appropriate rotation capability of the bandage or the wrapping material roll under the pressure, in another modified embodiment of the wrapping device 50, a roller/rollers may be further disposed between the clamping piece and the contact surface of the bandage or the wrapping material roll to exert the pressure on the bandage or the wrapping material roll, so as to improve the rotation capability of the bandage or the wrapping material roll under the tension adjustment. In addition, as shown in FIG. 13, the wrapping device 60 may be in a form that the clamping pieces 301 and 302 only constructed of partial frame, and the roller 308 is directly disposed between the frame of the clamping pieces 301 and 302. That is, the clamping pieces 301 and 302 exert the pressure on the roll body by closure through the roller 308, and the roller 308 is fixed on the frame 309 of the clamping pieces 301 and 302. In said arrangement, the roll body is pressed by the roller 308 in aid of rotating the roll body rather than pressed by a sheet-like structure. Therefore, it may be preferable to apply pressure to the wrapping material roll to obtain a desired tension when the wrapping is performed without hindering the unwinding of the wrapping material roll.

Apart from the tension-adjusting devices generating the tension by clamping the roll body, the wrapping device according to the embodiment of the present invention may also contain other kinds of tension-adjusting devices. For example, referring to FIG. 14, the wrapping device 70 may comprise a kind of tension-adjusting device 900 fixed on the connecting part 130 through one or more positioner 915. When the wrapping material roll is set in position, the tension-adjusting pressing plate 910 of the tension-adjusting device 900 separately disposed with respect to the connecting part 130 will correspond to the unfolded end of respective wrapping material roll (such as the wrapping material roll 310). As stated above, the tension-adjusting device 900 of FIG. 14 includes the tension-adjusting pressing plate 910 substantially parallel to the width of the wrapping material unfolded from the wrapping material roll, and the length of the tension-adjusting pressing plate 910 is the same with the width of the unfolded end of the wrapping material or is larger than the width of the unfolded end of the wrapping material. In addition, the tension-adjusting device 900 may include a set of retractable tension-adjusting springs 920 pressing and holding the tension-adjusting pressing plate 910.

In this case, pressure is applied by the tension-adjusting springs 920, and the tension-adjusting pressing plate 910 exert pressure on the unfolded end of the wrapping material roll 310, so as to obtain the desired tension of the bandage or the wrapping material 311. However, the present invention is not limited thereto, and in the mechanism applying the tension through indirectly pressing the bandage or the wrapping material by the tension-adjusting springs 920, the tension-adjusting pressing plate 910 may also be replaced by one of the tension-adjusting roller, or other spring pressing mechanisms.

Regarding to the above-described tension-adjusting device, the wrapping device of one of the preferred embodiments of the present invention may further comprise a tension controller provided at a position such as a handle for facilitating the operation of the operator. Tension controller allows the operator to adjust the tension in real-time to prevent from inappropriate tightness of wrapping, in which results in patient discomfort or insufficient fixation of wrapping. In one preferred embodiment, for example, the tension-adjusting device can be adjusted so that the average pressure of the bandage onto the contact surface of the skin is 18.2 mmHg. However, the above statement is merely an example, and the tension controller and the tension-adjusting device of the wrapping device of the present invention may be varied based on the demands. For example, provided that the desired purpose can be achieved or the affected area is not hurt upon wrapping, the average pressure in contact between the bandage and the skin may be 15 mmHg, 18 mmHg, 20 mmHg, etc., and the pressure can be adjusted in accordance with the patient's reaction and feeling and the operator's observation in real-time. In addition, the tension controller may be located on the handles, housings, or any other structures otherwise provided in the wrapping device.

Apart from the various embodiments shown above, the wrapping device of the present invention may be provided with various mechanical mechanisms or designs as desired, such as bearings, balls, etc.

The wrapping devices according to embodiments of the present invention can automatically or semi-automatically wrap the bandage in the affected area. In addition, the above-described wrapping device and the corresponding wrapping method can apply more than one bandages to perform the wrapping/bandaging at a time, therefore the bandaging results with multiple layers and multiple materials can be obtained after finishing one-time wrapping/bandaging. Further, in some preferred embodiments, the wrapping device of the present invention can adjust the bandage tension in real-time as if the wrapping is manually implemented by the medical staffs with hands Otherwise, the wrapping device of the present invention can circumferentially press the body part wrapped with the bandage by the pressing mechanism, as if the body part wrapped with the bandage is pressed, organized and flattened by the medical staffs. As stated above, the wrapping manner similar to, close to or preferred to the manual bandaging can help the medical staffs to wrap, and the wrapping may be implemented with reduction of manual intervention of medical staff or without the manual intervention of medical staff, thereby economizing the manpower or time required. When the wrapping device is applied in the emergency departments and the outpatient departments, it can make up for the problem of medical staff shortage, the workload of the medical staffs can be reduced, and the period through which the patient may suffer uncomfortable in the bandaging process may be reduced. Moreover, if a patient excludes and rejects to go to the hospital or is inconvenient to the hospital, the wrapping device which is easy to move and used can be operated alone or under the medical staff's assistance, therefore a desired bandaging and care can be done directly in the place where the patient stays (such as the home or the disaster scene). These advantages allow the medical staffs to have more time to deal with other medical situations, such as the emergency operation of patients in critical situation, therefore improving the efficiency of the overall Medicare Service System. In addition, qualities of the dressing or the fixation can be stabilized by the use of the wrapping device. Thus, great disparities in the quality of the wrapping or the fixation due to the experience of the medical staffs can be reduced, and the patients can be subjected to well medical care and treatment more evenly.

It is to be understood by those of ordinary skill in the art that, although many embodiments of the present invention are explained by substantially using gypsum fixation for instance in the specification, the present invention is not limited thereto. Accordingly, the present invention is also applicable in the normal medical bandage wrapping, the protective bandage wrapping, the exercise support bandage wrapping, or any other similar situations in which the irregular body parts need to be wrapped with flexible objects.

Although the present invention has been described with reference to the preferred embodiments thereof, it will be understood that the invention is not limited to the details thereof. Various changes and modifications in accordance with the appropriate technical solutions and technical concepts of the present invention should belong to the invention as claimed. Therefore, all such substitutions and modifications are intended to be embraced within the scope of the invention as defined in the appended claims.

What is claimed is:

1. A wrapping device for wrapping body parts, comprising:
    a rotation module, including:
        a first roller ring having a first ring hole surrounded and formed by a first inner ring wall;
        a second roller ring separately and coaxially disposed with the first roller ring and having a second ring hole surrounded and formed by a second inner ring wall; and
        a plurality of connecting parts, opposite ends of each of the plurality of connecting parts are separately connected to the first roller ring and the second roller ring;
    a driving module driving at least one of the first roller ring and the second roller ring to revolve; and
    at least a pressing device disposed on the second roller ring and protruding toward an inner space of the second ring hole.

2. The wrapping device according to claim 1, further comprising a wrapping module, wherein the wrapping module includes a plurality of wrapping material rolls positioned and nested axially on the plurality of connecting parts, respectively, and each of the plurality of wrapping material rolls comprises a wrapping material wound into a roll form.

3. The wrapping device according to claim 2, wherein the wrapping module further includes a shield disposed between two of the wrapping material rolls.

4. The wrapping device according to claim 1, wherein the plurality of connecting parts are inclined with respect to an axis passing through centers of the first roller ring and the second roller ring.

5. The wrapping device according to claim 4, wherein connection ends of the plurality of connecting parts attached on the first roller ring, the second roller ring, or both include a ball and socket joint or a groove, and the connection ends of the plurality of connecting parts attached on the first roller ring, the second roller ring, or both are provided with a preset degree of moving freedom through the ball and socket joint or the groove.

6. The wrapping device according to claim 1, further comprising a plurality of tension-adjusting devices disposed corresponding to and separated from the plurality of connecting parts at preset distances.

7. The wrapping device according to claim 6, wherein each of the plurality of tension-adjusting device includes a set of tension-adjusting springs, and one of a pressing plate, a roller, or a spring pressing mechanisms pressed and hold by the set of tension-adjusting springs, and the plurality of tension-adjusting devices are fixed on the plurality of connecting parts through one or more positioners.

8. The wrapping device according to claim 6, wherein the tension-adjusting device includes two clamping pieces capable of clamping toward each other, and the two clamping pieces are integrally formed or are connected with each other through one or more fasteners.

9. The wrapping device according to claim 1, wherein the driving module comprises:
    a motor; and
    a driving gear set having at least one gear;
    wherein at least one of the first roller ring and the second roller ring includes an external tooth structure, and the external tooth structure is engaged with the at least one gear.

10. The wrapping device according to claim 1, further comprising an accommodation module, wherein the accommodation module includes:
    a first housing part at least partially accommodating the first roller ring and enclosing a first opening corresponding to the first ring hole;
    a second housing part at least partially accommodating the second roller ring and enclosing a second opening corresponding to the second ring hole; and
    a connecting housing part located between the first roller ring and the second roller ring and connecting the first housing part and the second housing part, respectively,
    wherein the connecting housing part is located outside the same side of the first opening and the second opening.

11. The wrapping device according to claim 10, wherein the accommodation module includes a roller, outer peripheral surface of the first roller ring includes a track, the roller moves along the track and the side of the roller opposite to the track contacts against the first housing part when the first roller ring rotates.

12. The wrapping device according to claim 10, wherein the accommodation module includes a roller, outer peripheral surface of the second roller ring includes a track, the roller moves along the track and the side of the roller opposite to the track contacts against the second housing part when the second roller ring rotates.

13. The wrapping device according to claim 1, wherein the pressing device includes:
    a pressing end being proximity to the center of the second ring hole; and
    a spring structure with two ends being respectively connected to the pressing end and the second inner ring wall.

14. The wrapping device according to claim 13, wherein the pressing end of the pressing device is selected from the group consisting of a pressing ball, a pressing roller, and a smooth scraper having blunt edges, the spring structure has a support member and a spring member capable of compression and stretch, and a distance between the pressing end and the second inner ring wall is adjusted through the spring member.

\* \* \* \* \*